United States Patent [19]

Potter et al.

[11] Patent Number: 5,622,690
[45] Date of Patent: Apr. 22, 1997

[54] SEED-DERIVED PROTEINACEOUS COMPOSITIONS FOR REDUCTION OF SUNBURN CELL FORMATION

[75] Inventors: Richard Potter, Seeley Lake, Mont.; Peter T. Pugliese, Bernville, Pa.

[73] Assignee: Nurture, Inc., Missoula, Mont.

[21] Appl. No.: 145,328

[22] Filed: Oct. 29, 1993

Related U.S. Application Data

[63] Continuation-in-part of Ser. No. 31,611, Mar. 15, 1993, abandoned, which is a continuation-in-part of Ser. No. 505,126, Apr. 5, 1990.

[51] Int. Cl.$^6$ ............................................................... A61K 7/42
[52] U.S. Cl. ................................................. 424/59; 424/401
[58] Field of Search ............................................. 424/401, 59

[56] References Cited

U.S. PATENT DOCUMENTS

| | | | |
|---|---|---|---|
| 2,176,037 | 10/1939 | Musher | 426/543 |
| 2,876,164 | 3/1959 | Wershaw | 514/772.5 |
| 4,014,995 | 3/1977 | Juliano et al. | 514/783 |
| 4,211,801 | 7/1980 | Oughton | 426/430 |
| 4,220,287 | 9/1980 | Boczewski | 241/9 |
| 4,906,457 | 3/1990 | Ryan | 424/59 |
| 5,140,043 | 8/1992 | Darr et al. | 514/474 |
| 5,234,947 | 8/1993 | Cherksey | 514/449 |

FOREIGN PATENT DOCUMENTS

| | | |
|---|---|---|
| 2269974 | 5/1975 | France. |
| WO9115117 | 10/1991 | WIPO. |
| WO9421222 | 9/1994 | WIPO. |
| WO9418933 | 9/1994 | WIPO. |

OTHER PUBLICATIONS

Advertisement For "Kiss My Face" Non–Chemical Sunblock with Oat Protein Complex, Appearing in Longevity Magazine, Published Jul., 1994, p. 64.
Forssell, et al. "Comparison of Methods for Separating Polar Lipids from Oat Oil" Fat Sci. Technol. 94(9): 355–358 (1992).
Toda, et al. "Electron Microscopic Observations in Human Skin After Psoralen Photosensitization" Sunlight and Man pp. 419–430 (Tokyo Press, 1974).
Food and Drug Administration's Advance Notice of Proposed Rulemaking on OTC Sunscreen Products. Federal Register 43(166): 38206–38269 (1978).
Berger, D.S. "The Sunburning Ultraviolet Meter: Design and Performance" Photochemistry and Photobiology 24: 587–593 (1976).
Bowman, K. "Global Trends in Total Ozone" Science 239: 48–50 (1988).
Cooper, et al. "Effect of UV Light on Induction of Immune Response to Epicutaneous Antigen in Humans" FASEB J. 5: A967.
Daniels, et al. "Histochemical Responses of Human Skin Following Ultraviolet Irradiation" J. of Invest. Dermatology 37: 351–357 (1961).

Elmets, C. "Cutaneous Photocarcinogenesis" Pharmacology of the Skin, Boca Raton, Florida; Mukhair, H. ed. CRC Press 389–416 (1992).
Elmets, et al. "Analysis of the Mechanism of Unresponsiveness Produced by Haptens Painted on Skin Exposed to Low Dose Ultraviolet Radiation" J. Exp. Med. 158: 781–794 (1983).
Elmets, et all. "Differential Distribution of Langerhans Cells in Organ Culture of Human Skin" J. of Invest. Dermatology 79(4): 340–345 (1982).
Elmets, et al. "Photoprotective Effects of Sunscreens in Cosmetics on Sunburn and Langerhans Cell Photodamage" Photodermatology, Photoimmunology, Photomed. 9: 113–120 (1992).
Epstein, et al. "Effects of 8–Methoxypsoralen–Induced Phototoxic Effects on Mammalian Epidermal Macromolecule Synthesis" In Vivo Photochemistry & Photobiology 21: 325–330 (1975).
Garmyn, et al. "Modification of Sunburn Cell Production in 8–MOP Sensitized Mouse Epidermis: A Method of Assessing UVA Sunscreen Efficacy" Society for Invest. Dermatology 92(4): 642–645 (1989).
Gilchrest, et al. "The Human Sunburn Reaction: Histologic and Biochemical Studies" J. of Am. Acad. Dermatol. 5: 411–422 (1981).
Kapsenberg, et al. "Langerhans Cells: A Unique Subpopulation of Antigen Presenting Dendritic Cells" Skin Immune System (SIS), Boca Raton, Florida; CRC Press, 1990; 109–124.
Kiistala, et al. "Dermo–Epidermal Separation with Suction" J. of Invest. Dermatology 48(5): 466–477 (1967).
Koh, et al. "Sunlight and Cutaneous Malignant Melanoma: Evidence for and Against Causation" Photochemistry & Photobiology 51(6): 765–779 (1990).
Kripke, M. "Impact of Ozone Depletion on Skin Cancers" J. Dermatol. Surg. Oncol. 14(8): 853–857 (1988).
Krutman,, et al. "Recent Studies on Mechanisms in Photoimmunology" Photochemistry & Photobiology 48(6): 787–798 (1988).
Rae, et al. "An Ultraviolet B Radiation Protocol for Complete Depletion of Human Epidermal Langerhans Cells" J. Dermatol. Surg. Oncol. 15: 1199–1202 (1989).

(List continued on next page.)

Primary Examiner—John C. Bleutge
Assistant Examiner—Robert H. Harrison
Attorney, Agent, or Firm—Knobbe, Martens, Olson & Bear LLP

[57] ABSTRACT

A composition comprising a seed-derived proteinaceous particulate material for reducing the formation of sunburn cells in skin exposed to ultraviolet irradiation and method of using same, where the seed-derived material has a protein content of between about 1% and 50% and an average particle size of between about 1.0 μm and about 600 μm. Seed-derived proteinaceous particulate material is applied to skin in a topically acceptable carrier and reduces the formation of sunburn cells upon exposure of the skin to ultraviolet irradiation.

8 Claims, No Drawings

OTHER PUBLICATIONS

Rosario, et al. "Histological Changes Produced in Skin by Equally Erythemogenic Doses of UV–A, UV–B, UV–C and UV–A with Psoralens" British J. of Dermatology 101: 299–308 (1979).

Sambuco, C.P. "Miniature Swine as an Animal Model in Photodermatology: Factors Influencing Sunburn Cell Formation" Photodermatology 2: 144–150 (1985).

Toews, et al. "Epidermal Langerhans Cell Density Determines Whether Contact Hypersensitivity or Unresponsiveness Follows Skin Painting with DNFB" J. of Immunology 124(1): 445–453 (1980).

Woodcock, et al. "The Sunburn Cell in Mouse Skin: Preliminary Quantitative Studies on its Production" British J. of Dermatology 95: 459–468 (1976).

Yoshikawa, et al. "Susceptibility to Effects of UVB Radiation on Induction of Contact Hypersensitivity as a Risk Factor for Skin Cancer in Humans" Society for Invest. Dermatology 95(5): 530–536 (1990).

Young, A. "The Sunburn Cell" Photodermatology 4: 127–134 (1987).

Young, et al. "An Action Spectrum for 8–MOP Induced Sunburn Cells in Mammalian Epidermis" British J. of Dermatology 104: 541–548 (1981).

Young, et al. "The Sunburn Cell in Hairless Mouse Epidermis: Quantitative Studies with UV–A Radiation and Mono– and Bifunctional Psoralens" J. of Invest. Dermatology 79(4): 218–221 (1982).

"Longevity", Jul. 1994.

SEED-DERIVED PROTEINACEOUS COMPOSITIONS FOR REDUCTION OF SUNBURN CELL FORMATION

CROSS REFERENCE TO RELATED APPLICATIONS

The present application is a continuation-in-part of U.S. patent application Ser. No. 08/031,611, filed Mar. 15, 1993 (now abandoned), which is a continuation-in-part of copending U.S. patent application Ser. No. 07/505,126, filed Apr. 5, 1990 pending.

BACKGROUND OF THE INVENTION

1. Field of the Invention

The present invention relates to the use of proteinaceous materials for use in protection of skin from the generation of sunburn cells in response to ultraviolet radiation.

2. Description of the Prior Art

In recent years, it has become increasingly apparent that cutaneous exposure to solar ultraviolet (UV) radiation mediates a number of harmful effects in the human body. Chronic UV exposure is a well-recognized etiological agent for cutaneous squamous cell and basal cell carcinoma. Elmets *Pharmacology of the Skin,* Boca Raton, Fla.; CRC Press, 389–416 (1992). Further, UV exposure may play a role in promoting the development of malignant melanomas. Kob KH, et al. "Sunlight and Cutaneous Melanoma: Evidence for and Against Causation," *Photochem. Photobiol.* 31:765–779 (1990). Histopathologically, acute UV exposure causes solar erythema (sunburn) and is associated with the development of dyskeratotic cells within the epidermis (sunburn cells), a parameter that may reflect UVB-induced DNA damage. Daniels F Jr, et al. "Histochemical Response of Human Skin Following Ultraviolet Irradiation" *J. Invest. Dermatol.* 37:351–357 (1961); Gilchrest BA, et al. "The Human Sunburn Reaction: Histologic and Biochemical Studies" *J. Am. Acad. Dermatol.* 5:411–422 (1981).

Recent studies also indicate that UVB radiation can profoundly influence the immune response. Krutmann J, et al. "Recent Studies on Mechanisms in Photoimmunology" *Photochem. Photobiol.* 48:787–798 (1988). In particular, UV radiation has an inhibitory effect on epidermal Langerhans cells. Gilchrest BA, et al. supra; Tocwa GB, et al. "Epidermal Langerhans Cell Density Determine Whether Contact Sensitivity or Unresponsiveness Follows Skin Painting with DNFB" *J. Immunol.* 124:445–453 (1980); Rae V, et al. "An Ultraviolet B Radiation Protocol for Complete Depletion of Human Epidermal Langerhans Cells" *J. Dermatol. Surg. Oncol.* 15:1199–1202 (1989). Langerhans cells represent approximately 2–4% of the entire epidermal population and are essential for the activation and expansion of helper T lymphocytes, an obligatory step in the initiation of immune responses. Kapienberg ML, et al. "Langerhans Cells: A Unique Subpopulation of Antigen Presenting Dendrille Cells" In: Bos, JD, ed. *Skin Immune System (SIS),* Boca Raton, Fla.; CRC Press, 1990; 109–124. When murine skin is exposed to 200–700 $J/m^2$ UVB radiation daily for 4 consecutive days, there is a marked reduction in the number of epidermal ATPase-positive Langerhans cells. A reduction in the capacity to initiate cell-mediated immune responses through UV-irradiated skin (Tocwa, GB, et al. supra.) and the induction of suppressor T lymphocytes (Elmets CA, et al. "Analysis of the Mechanism of Unresponsiveness Produced by Haptens Painted on Skin Exposed to Low Dose Ultraviolet Radiation" *J. Exp. Med.* 158:781–794 (1983)) is also observed. Recent studies indicate that UVB radiation has similar effects in humans. Yoshikawa T, et al. "Susceptibility to Effects of UVB Radiation on Induction of Contact Hypersensitivity as a Risk Factor for Skin Cancer in Humans" *J. Invest. Dermatol.* 95:530–536 (1990); Cooper KD, et al. "Effect of UV Light on Induction of Immune Response to Epicutaneous Antigen in Humans" FASEB J. 5:A967.

Because humans are exposed to increasing amounts of UV radiation during outdoor recreational activities than in the past (Bowman KP "Global Trends in Total Ozone" Science 239:48–50 (1988); Kripke ML "Impact of Ozone Depletion on Skin Cancers" *J. Dermatol. Surg. Oncol.* 14:853–857 (1988)), efforts have been made to incorporate sunscreening agents into topical cosmetic products in an attempt to block the adverse clinical, histological and immunological effects of UV radiation exposure on the skin. For example, recent work has indicated that certain extracts from natural products have the ability to reduce the production of sunburn cells and may have an immunostimulating effect on Langerhans cells. E.g., Elmets CA, et al. "Photoprotective Effects of Sunscreens in Cosmetics on Sunburn and Lanngerhans Cell Photodamage" *Photodermatol. Photoimmunol. Photomed.* 9:113–120 (1992).

SUMMARY OF THE INVENTION

In accordance with a first aspect of the present invention, there is provided a topical formulation for inhibiting sunburn cell production in skin exposed to ultraviolet radiation, comprising an amount of a free flowing seed derived material having a protein content of between about 1% to 50% and an average particle size of from about 1.0 μm to 600 μm effective to inhibit sunburn cell formation in skin upon exposure to ultraviolet radiation relative to untreated skin in a topically acceptable carrier. Preferably, the material is derived from grinding the seeds and extracting lipids from the resulting ground material with an organic solvent. The average particle size of the material is preferably between 1 to 300 μm, or more preferably between 1–10 μm. In another embodiment, the average particle size of the material is between 300–600 μm.

The seeds are preferably selected from the group consisting of legumes and grains, particularly, from the group consisting of canola, beans, rape seed, soya, and barley, or more preferably oats.

In a highly preferred embodiment, the material is heated to a temperature of at least 60° C. prior to incorporation in the formulation.

In accordance with another aspect of the present invention, there is provided a method for inhibiting the formation of sunburn cells in skin, comprising applying the topical formulation, described above, to skin prior to exposing the skin to ultraviolet radiation. Preferably, the formulation is heated to a temperature of at least 60° C. prior to application to the skin.

In accordance with another aspect of the present invention, there is provided a method for inhibiting the formation of sunburn cells in skin when the skin is exposed to ultraviolet radiation, comprising applying a composition including a sunburn cell protective amount of a substantially chemically intact proteinaceous particulate material derived from seeds in a topically acceptable carrier to the skin prior to exposure to ultraviolet radiation. In this embodiment, the seeds are preferably selected from the group consisting of legumes and grains, particularly, canola, beans, rape seed, soya, and barley, and preferably oats.

In a preferred embodiment, the proteinaceous material is derived from grinding the seeds and extracting lipids from the resulting ground material with an organic solvent.

In a highly preferred embodiment, the formation of sunburn cells is reduced by greater than about 50 percent relative to untreated skin.

In another preferred embodiment, the proteinaceous particulate material is heated to about 60° C. prior to incorporation in the carrier.

DETAILED DESCRIPTION OF THE PREFERRED EMBODIMENTS

The present invention relates to the use of a proteinaceous particulate material for protecting skin from the generation of sunburn cells following exposure to ultraviolet ("UV") radiation. Preferably, the proteinaceous particulate material is a substantially chemically intact material that is derived from seeds. For example, virtually any seed can be used as the starting material, such as those from legumes and grains, for instance, canola, barley, beans, oats, rape seed, and soya. However, oats are highly preferred.

The seed materials are preferably milled, extracted with an organic solvent (to remove lipids), and dried in order to form the proteinaceous particulate materials for use in the present invention. Oughton, in U.S. Pat. No. 4,154,728, describes a process for separating fractions of differing compositions from comminuted proteinaceous material from a variety of food sources, including wheat, rye, barley, triticale, peas, and buckwheat. The Oughton process comprises mixing the proteinaceous material with an aliphatic hydrocarbon or alcohol suitable to dissolve the lipids in the material. The wet slurry is distributed by means of centrifugation into fractions which differ primarily in protein composition, as well as starch composition. A similar process is applied to comminuted oats in U.S. Pat. Nos. 4,211,695 and 4,211,801, also to Oughton.

To facilitate recovery of the protein, in particular, from the slurry produced in accordance with the foregoing processes, U.S. Pat. Nos. 4,208,295 and 4,208,260 to Oughton disclose the application of an electric field to the mixture in collection of a comminuted oat fraction which clings to the anode. An improved method of recovery is disclosed in U.S. Pat. No. 4,407,841 to Boocock, comprising the addition of aqueous ethanol to the slurry to agglomerate the proteinaceous material and to facilitate the separation thereof.

It is preferred that the proteinaceous particulate materials of the present invention be prepared in a non-aqueous environment, and that the extraction be conducted with a nonpolar solvent, such as hexane. If water is used in the process, some changes to the protein structure may occur. These changes may be at least partially reversed by freeze drying (lyophilization) of the product. Heat is also deleterious, resulting in permanent changes in the properties of the proteinaceous emulsifying agents.

Accordingly, the proteinaceous particulate material is prepared by separating the protein and starch from lipids in the seed with organic solvents, such as propanol, ethanol, or hexanes, and most preferably, hexanes. This process removes the lipids and allows separation of other insoluble materials. The solvents are preferably nontoxic or removed prior to the use of the materials. After the extraction of lipids and separation of the proteinaceous materials, the particles are separated to a desired particle size or range of sizes.

As a consequence, subsequent milling and/or separation steps are often necessary after extraction of the lipids and other undesired materials. Such milling and separation steps may be accomplished according to many processes that are conventional to, and well known in the art. Proteinaceous emulsifying agents that are derived from natural seeds, such as grains and legumes, are often irregular in shape due to crushing and fragmenting during the milling process. However, median particle size can be determined by milling parameters or by using a series of graduated sieves or through particle size analysis. Furthermore, in applications requiring more exacting control over the particle sizes, more advanced particle sizing apparatus and methods are available to those of skill in the art, such as gravimetric analyses or digital imagery sizing.

The proteinaceous particulate materials are advantageously dried prior to use to remove solvent and other indigenous volatiles. In addition, depending upon the protein separation process, residual solvent could reside in the interstices of the particulate which could cause skin irritation.

Drying can be accomplished by any number of known techniques, such as fluid bed drying or subjecting the powder to a vacuum with or without the addition of heat. Often, however, in the case of the proteinaceous particulate materials of the present invention, sufficient desolventization may be accomplished through air drying.

The proteinaceous materials so prepared are highly effective as emulsifying agents. For example, when they are combined with an aqueous phase and a lipophilic phase, an oil-in-water or a water-in-oil emulsion can be formed spontaneously at room temperature and with minimal agitation.

A highly beneficial aspect of the proteinaceous materials is that they are totally natural and are extremely safe to use. In contrast, conventional emulsifying agents carry some risk of skin irritation, when applied topically.

Accordingly, the present invention makes use of the above emulsifying properties of the proteinaceous materials to prepare formulations that are capable of topical application. As described in copending U.S. patent application Ser. Nos. 07/505,126 and 08/031,611, now abandoned, the topical formulations can be used as, or in, sunscreen formulations. The proteinaceous emulsifying agents naturally possess sun protective qualities because of their composition and particulate structure. Thus, it is possible to prepare a sun protective formulation through simply mixing the emulsifying agents in a lipophilic base and then introducing an aqueous phase, followed by agitation to form the final composition. Furthermore, we have unexpectedly discovered that sunscreen formulations prepared with the proteinaceous materials, when applied to the skin, act to control the generation of sunburn cells when the skin is subjected to UV radiation.

As discussed above, it has become increasingly apparent that exposure to the sun can be harmful. For example, there are clear signs that exposure to the sun increases a person's chances to get a variety of cancers, particularly skin cancer. In response, there have been substantial efforts invested in developing effective sun protectant formulations that will protect the skin from the deleterious effects of the sun.

As previously described, proteinaceous materials of the present invention can be used to prepare a sunscreen formulation through emulsifying a lipophilic phase and an aqueous phase with the proteinaceous materials. Following this procedure, a sun protective formulation having a sun protection factor ("SPF") of greater than approximately 1, and often 2, can be prepared. An SPF value is defined as the UV energy required to produce a minimal erythemal dose ("MED"), or redness, on protected skin divided by the energy to produce an MED on unprotected skin. This SPF system essentially allows the calculation of the additional time that a person wearing a sunscreen product can remain in the sun without burning. As such, an SPF of 2 allows a user to stay in the sun twice as long, whereas an SPF of 15 increases the relative time to 15 times as long.

The SPF value of the compositions prepared in accordance with the invention can be easily varied through the addition of other materials. For example, titanium dioxide ($TiO_2$) is a particularly effective material to increase the SPF of the compositions. A sunscreen formulation containing only 6% $TiO_2$ attains an SPF of approximately 9.6. With the addition of 12% of a proteinaceous emulsifier as prepared from the fines in accordance with the following protocol an SPF of 11.6 is attained.

A proteinaceous particulate emulsifier having a 10–20% protein content and an average particle size of 1–10 μm was prepared as follows:

Dried oats were ground using conventional techniques. Specifically, the ground materials were collected and placed in a vat containing hexane and stirred for between 0.25 to 5 hours. As will be understood, in the grinding process, a broad spectrum of particle sizes are formed, from "fines" to "roughs," which are separated, one from the others, through conventional sieving apparatus. The fines had a particle size range from about 1 to about 300 μm with the majority being in the 1–10 μm range, and the roughs had a particle size range from about 300 to about 600 μm.

Generally, fines are suitable for refined emulsion preparation, and roughs may be appropriately used for other applications. The hexane solubilized the lipids from the particles.

Thereafter, the solution was centrifuged at 4500× g to layer out the insoluble proteinaceous materials. Next, the hexane was removed via centrifugation and the solid materials were air dried at room temperature and reduced humidity (i.e., relative humidity not exceeding 50 percent). Care was taken to ensure that the entire process remained relatively anhydrous.

I. CALCULATION OF SPF VALUES

In order to determine the sunscreen protection factor (SPF) values of the sunscreen formulations, we undertook studies on twenty-five human subjects when exposed to simulated sunlight. The subjects were healthy females between the ages of 21 and 65, with a mean age of 44.6. All subjects signed an informed consent form. The subjects were selected after determination of skin type. Skin types were determined as shown in the following Table:

TABLE I

| SKIN TYPE | DESCRIPTION |
| --- | --- |
| Type I | Always Burns Easily; Never Tans (Sensitive) |
| Type II | Always Burns Easily; Tans Minimally (Sensitive) |
| Type III | Burns Moderately; Tans Gradually (Light Brown), (Normal) |
| Type IV | Burns Minimally; Always Tans Well (Moderate Brown) |
| Type V | Rarely Burns; Tans Profusely (Dark Brown), (Insensitive) |
| Type VI | Never Burns; Deeply Pigmented (Insensitive) |

A. Methods and Materials

The method we used was similar to the procedure outlined by the FDA in the OTC Monograph on Sunscreen Products. See *Food and Drug Administration's Advance Notice of Proposed Rulemaking on OTC Sunscreen Products*, published in the Federal Register, Vol. 43, No. 166, Pages 38206–38269, Aug. 25, 1978. The solar simulator (Solar Light Company, Philadelphia, Pa.) was made of a 150 Watt compact arc xenon burner with a power supply, an ignitor, and filters. Infrared radiation was attenuated by filtration with Corning Black glass and a dichromic mirror. See Berger, D. S., "The Sunburning Ultraviolet Meter: Design and Performance," *Photochem. Photobiol.*, 24:587–593, (1976). Short wave ultraviolet was eliminated by external filtration with a 1 mm thickness WG320 glass (Schott Filter Co., Duryea, Pa.). The radiation output was measured with a portable R-B meter before and after testing.

Subjects reported to the laboratory and were selected after determination of their skin type (see Table I). The area to be tested was the back, between the scapulae and the beltline, lateral to the midline. Five graduated time exposures (25% increments) were made to unprotected skin to determine the MED (minimal erythema dose). Twenty four hours after irradiation, the erythema of each site was evaluated. The shortest exposure time for perceptible erythema was recorded as the MED. Test sites on each subject consisted of a 40 $cm^2$ area, subdivided into four equal squares, were marked with indelible ink on the subject's back. In addition to the test and control sites another MED determination (unprotected control) was made.

Each test formulation was tested on five (5) subjects. Control formulations were tested on all subjects. A 0.1 ml amount of each test and control formulation was applied to each site and was spread evenly. Exposure time was determined for each subject based on their MED and the expected SPF of the test and control formulations. The exposure times were selected so that the third site would receive the dose expected to produce the minimal erythema dose. All sites were examined at 22±2 hours after exposure for the minimal perceptible erythema present at the test and control sites.

The SPF for each test and control formulation was calculated as follows:

$$SPF = \frac{MED \text{ Treated Skin}}{MED \text{ Untreated Skin}}$$

In the following Tables, a variety of formulations of the present invention and their SPF values are provided:

TABLE II

| Ingredient | Formula No. | | | | | | | | |
|---|---|---|---|---|---|---|---|---|---|
| | 1 | 2 | 3 | 4 | 5 | 6 | 7 | 8 | 9 |
| Proteinaceous Emulsifier 1 | 12 | 12 | 12 | — | — | — | — | — | — |
| Proteinaceous Emulsifier 2 | — | — | — | — | — | — | 2 | 2 | 2 |
| TiO₂ | 15 | — | — | 15 | — | — | 15 | — | — |
| Presperse M262 | — | 6 | — | — | 6 | — | — | 6 | — |
| Creative Polymer Hph | — | — | 6 | — | — | 6 | — | — | 6 |
| Rice Bran Oil | 5 | 5 | 5 | 5 | 5 | 5 | 5 | 5 | 5 |
| Elefac | 6 | 9 | 9 | 12 | 15 | 15 | 10 | 15 | 15 |
| Finsolv T | 5 | 11 | 11 | 11 | 16 | 16 | 11 | 16 | 16 |
| Pemulan T2 | 0.2 | 0.2 | 0.2 | 0.2 | 0.2 | 0.2 | 0.2 | 0.2 | 0.2 |
| Arlacel 83 | 0.5 | 0.5 | 0.5 | 0.5 | 0.5 | 0.5 | 0.5 | 0.5 | 0.5 |
| Water | 54 | 54 | 54 | 54 | 54 | 54 | 54 | 54 | 54 |
| Keltrol | 0.15 | 0.15 | 0.15 | 0.15 | 0.15 | 0.15 | 0.15 | 0.15 | 0.15 |
| NaOH 50% | 0.1 | 0.1 | 0.1 | 0.1 | 0.1 | 0.1 | 0.1 | 0.1 | 0.1 |
| Germaben 2e | 1 | 1 | 1 | 1 | 1 | 1 | 1 | 1 | 1 |
| Phenoxyethanol | 0.5 | 0.5 | 0.5 | 0.5 | 0.5 | 0.5 | 0.5 | 0.5 | 0.5 |
| SPF Value | 11.6 | 9.3 | 10.3 | 9.6 | 11 | 8.6 | 10.3 | 8.6 | 8.3 |

TABLE III

| Ingredient | Formula No. | | | | | |
|---|---|---|---|---|---|---|
| | 1 | 2 | 3 | 4 | 5 | 6 |
| Proteinaceous Emulsifier 1 | 12 | 12 | 6 | 6 | 6 | 6 |
| Proteinaceous Emulsifier 2 | — | — | 2 | 2 | — | 1 |
| TiO₂ | 6 | 6 | 6 | 6 | 6 | 6 |
| PTFE | 3 | — | 3 | 3 | 3 | 3 |
| Octyl Stearate | 5 | 8 | 8 | 6 | 8 | 8 |
| Isostearyl Palmitate | 4 | 4 | 4 | 4 | 4 | 3 |
| Elefac | 3 | 3 | 7 | 7 | 7 | 10 |
| Abil Wax 9801 | 2 | 2 | 2 | 2 | 2 | 2 |
| Water | 58 | 58 | 58 | 58 | 58 | 58 |
| Glycerine | 2 | 2 | 2 | 2 | 2 | 2 |
| Germaben 2e | 1 | 1 | 1 | 1 | 1 | 1 |
| Parsol MCX | — | — | — | 2 | — | 4 |
| WE09 | 5 | 5 | 5 | 5 | 5 | 5 |
| Iron Oxide | — | — | — | — | — | 0.14 |
| SPF Value | 12 | 15 | 15 | 15 | 15 | 15 |

It will be appreciated, however, that the SPF system only measures protection from some UVB rays (290–320 nm). Low UVB (280–290 nm), UVA (320–400 nm) and UVC (less than 280 nm) are not well blocked by, or calculated in, the SPF system of sunscreen activity. Moreover, it will be understood that UVA rays are thought to be the radiation that is primarily responsible for long-term cumulative effects, such as basal skin cell carcinomas and the more lethal squamous cell carcinomas. Traditional screens, generally, do not effectively block UVA rays. Titanium dioxide can be added to enhance UVA protection.

Nevertheless, whenever skin is burned by the sun (solar erythema), the skin exhibits a number of histological changes. Dyskeratotic cells (sunburn cells) form within the epidermis. A sunburn cell is an epidermal cell with an eosinophilic (clear) cytoplasm and either no nucleus or a contracted, irregular nucleus, when stained with hematoxylin and eosin. The formation of sunburn cells may indicate the occurrence of UVB induced DNA damage.

Further, it is also predicted that the UVB radiation has an effect on immune response. This is exhibited by the inhibition of Langerhans cells. Langerhans cells represent approximately 2–4% of the total epidermal cell population and are critical to the activation and expansion of helper T-cell lymphocytes. The activation and expansion of helper T-cells is a fundamental step in immune system cascade in epidermal tissue.

Unexpectedly, the proteinaceous materials of the present invention when applied to the skin, either in an emulsion or in some other topical form, act to prevent the formation of sunburn cells. This indicates that the materials are preventing damage, presumably to the DNA, in the cells. There is also some evidence that the proteinaceous materials act to prevent the inhibition of Langerhans cells, thus, preserving normal immune response. Moreover, the proteinaceous materials do not necessarily have to be used in emulsions to be effective. Rather, the materials can be merely added to any topically acceptable formulation in an amount effective to protect against the formation of sunburn cells. However, formulation in an emulsion is preferred.

Moreover, it was also discovered that the sunburn cell protective nature of the materials could be maximized as well as varied. In particular, proteinaceous material using the roughs prepared in accordance with the protocol described on page 6 were found to have superior sunburn cell protective effects. Further, when these materials were prepared and heated to a temperature of at least 60° C., prior to incorporation in a sunscreen, enhanced protection was observed. To heat the proteinaceous materials, the materials were dispersed in a saline solution in a beaker and the beaker placed in a preheated water bath at the desired temperature and allowed to heat for about 20 minutes. The enhanced protective effects are demonstrated in connection with the proteinaceous emulsifier 2 material that was prepared using the roughs prepared in accordance with Example I in U.S. patent application Ser. No. 08/031,611 and heated to greater than 60° C. Such materials are discussed in the following Tables and in the Appendices. Similarly, sunscreen formulations could be prepared and heated to a temperature of at least 60° C. prior to application to the skin and similar results were observed.

Preferably, the observed sunburn cell inhibition through use of the compositions and the method of the present invention is at least 2% relative to untreated skin. However, inhibitions up to and exceeding 95% relative to untreated skin have been observed. Accordingly, in preferred embodiments, sunburn cell inhibition is between 2 and 100% relative to untreated skin. Common inhibitions of between 22 and 95% relative to untreated skin are often achieved.

In order to test the inhibition of sunburn cell production, a variety of sunscreen formulations were prepared in accordance with the following discussion. Different preparations were made for use with testing UVA and UVB response. In connection with the UVA studies, we prepared a number of sunscreen emulsion formulations as shown in Appendices I and II.

II. SUNBURN CELL PRODUCTION

We next looked at the ability of the various compositions to protect against sunburn cell generation in response to both UVA and UVB radiation.

A. Experiment I

1. UVA Studies

In the first experiment, sunscreen formulations were tested in the hairless mouse model for their protective effects against the formation of sunburn cells (SBC's) when the mice are treated with a phototoxic agent 8-methoxypsoralens (8-MOP) prior to UVA irradiation. The "sunburn cell" (SBC) appears in mammalian epidermis after exposure to ultraviolet radiation. When stained with hematoxylin and eosin, the cell has a pyknotic nucleus and shrunken, glassy, eosinophilic cytoplasm. Daniels et al. "Histochemical responses of human skin following ultraviolet irradiation" *J. Invest. Dermatol.* 37:351–357 (1961), Young "The sunburn cell" *Photodermatology* 4:127–134 (1987), Woodcock et al. "The sunburn cell in mouse skin: preliminary quantitative studies on its production" *Br. J. Dermatol.* 95:459–468 (1976). SBC production is dose and wavelength dependent. Young, supra, Woodcock et al., supra, Sambuco "Miniature swine as an animal model in photodermatology: factors influencing sunburn cell formation" *Photodermatology.* 2:144–150 (1985). 8-MOP in combination with UVA radiation induced SBC's. Young, supra, Woodcock et al., supra, Epstein et al. "8-methoxypsoralen induced phototoxic effects on mammalian epidermal macromolecule synthesis in vivo" *Photochem. Photobiol.* 2:325–330 (1975), Young et al. "An action spectrum for 8-MOP induced sunburn cells in mammalian epidermis" *Br. J. Dermatol.* 104:541–548 (1981), Young et al. "The sunburn cell in hairless mouse epidermis quantitative studies with UVA radiation and mono and bifunctional psoralens" *J. Invest. Dermatol.* 79:218–222 (1982), Rassario et al. "Histological changes produced in skin by equally erythemogenic doses of UVA, UVB, UVC, and UVA with psoralens" *Br. J. Dermatol.* 101:229–308 (1979), Toda et al. "Electron microscopic observations in human skin after psoralen photosensitization" In: Fitzpatrick et al. (eds). *Sunlight and Man* pp. 419–430 (Tokyo University of Tokyo Press, 1974). The number of SBC's was used to quantify the UVA screening efficacy of products in 8-MOP sensitized mouse epidermis. Garmyn et al. "Modification of sunburn cells production in 8-MOP sensitized mouse epidermis: a method of assessing UVA sunscreen efficacy" *J. Invest. Dermatol.* 92:642–645, 1989. Photoplex (Herbert Laboratories) and a Homosalate Standard were used as the control formulations.

a. Materials and Methods

A detailed review of the protocol used in our experiments is also provided in Garmyn et al. "Modification of Sunburn Cell Production in 8-MOP Sensitized Mouse Epidermis: A Method of Assessing UVA Sunscreen Efficiency" *J. Invest. Dermatol.* 92:642–645 (1989), the disclosure of which is hereby incorporated by reference.

Hairless albino mice (SKH/hr) were used in these studies, with two animals per experiment. Mice were maintained in a room with controlled ventilation and constant monitoring of temperature and humidity. The room light was cycled every 12 hours, dark and light, with an automatic timer. Mice were housed in plastic cages (Fisher, Pittsburgh, Pa.) and fed Purina Mills Mouse Chow #5105 ad lib. Special cages were built at our facility to house 1–2 mice per 30 sq. in. and allowed for free ranging by the mice. The bedding (pine shavings purchased at Agway, Bernville, Pa.) and water was removed during irradiation. Immediately after irradiation, water was resupplied.

In the studies, the following light sources were used Source 1: 150 Watt Compact Arc (Solar Light Co., Philadelphia, Pa. 19126, #24); Source 2: Panasonic Blacklight, F40BL/(T-10); Source 3: FS40T12 light sources, UVB, 9107. In connection with these light sources, spectradiometric assessments were done as follows: Source 1: no additional filtration, with the attached filter, with a WG320/1 mm filter, and with a WG345/1 mm filter; Source 2: spectradiometric assessment will be done on this source without additional filtration; Source 3: spectradiometric assessment will be done without filtration and with a cellulose acetate filter (clear acetate—0.005 inches), (Plastic Suppliers, Blackwood, N.J. 08012).

In the UVA studies, UVR light Source 3 was chosen for use and the light intensity was measured with an IL1700 Radiometer.

b. Procedure

Crystalline 8-MOP (Sigma Chemical Co., St. Louis, Mo.) was dissolved in 90% ethanol (Sigma Chemical Co.) to a concentration of 0.05%. Two hundred μl of the 8-MOP solution was pipetted onto the back of each mouse and spread evenly. To ensure adequate 8-MOP penetration, the products were applied 45 minutes after 8-MOP application.

500 μl of product was pipetted and rubbed on evenly to the back of each mouse in approximately a 16 cm$^2$ area. An untreated grid on the animals served as the control. Fifteen minutes after product application, the animals were exposed to UVA radiation of one MED (minimal erythema dose).

Twenty-four hours post-irradiation, the mice were sacrificed by cervical dislocation. Skin samples, 1"×1", were taken from the irradiated area of the back. Samples were sent for histology to American Medical Laboratories, Inc., Fairfax, Va. 22030 and stained with hematoxylin and eosin. SBC's were counted at a magnification of 40×. At least 20 different fields of view (20×0.5 mm) were counted to obtain the number of SBC's per sample.

c. Results

The results from the experiments are provided in the following Tables IV and V. In both of the Tables, the number of sunburn cells in the skin of UVA irradiated mice is provided. The mice were irradiated as described above, with or without prior application of the indicated sunscreen formulation. Each experimental test group contained five mice, designated A, B, C, D, and E.

A Protective Index (% reduction of SBC formation) was calculated as:

$$\text{Protective Index} = \frac{(\text{Irradiated Untreated} - \text{Product})}{(\text{Irradiated Untreated})} \times 100$$

TABLE IV

| Animal | Irradiated No 8-MOP No sunscreen | 8-MOP No sunscreen | 8-MOP Hom. Std. | 8-MOP Photoplex | 8-MOP 302 | 8-MOP 303 | 8-MOP 307 |
|---|---|---|---|---|---|---|---|
| A | 50 | 74 | 29 | 07 | 18 | 42 | 156 |
| B | 45 | 81 | 42 | 38 | 57 | 45 | N/A |
| C | 37 | 94 | 29 | 26 | 31 | 36 | 65 |
| D | 41 | 130 | 31 | 25 | 38 | 40 | 172 |
| E | 28 | 97 | 40 | 07 | 33 | 26 | 136 |
| TOTAL | 201 | 476 | 171 | 103 | 177 | 189 | 529 |
| MEAN | 40 | 95 | 34 | 21 | 35 | 38 | 132 |
| PERCENT REDUCTION | — | — | 64% | 78% | 63% | 60% | (39%) |

N/A - Not available.

TABLE V

| Animal | 8-MOP 3016 | 8-MOP 3017 | 8-MOP 3018 | 8-MOP 3019 | 8-MOP 23-3 | 8-MOP 29-1 |
|---|---|---|---|---|---|---|
| A | 05 | 22 | 08 | 05 | 16 | 14 |
| B | 09 | 04 | 06 | 21 | 35 | 14 |
| C | 08 | 14 | 21 | 02 | 26 | 13 |
| D | 03 | 26 | 15 | 14 | 30 | 11 |
| E | 19 | 24 | 11 | 27 | 12 | 11 |
| TOTAL | 44 | 90 | 61 | 69 | 119 | 63 |
| MEAN | 09 | 18 | 12 | 14 | 24 | 13 |
| PERCENT REDUCTION | 91% | 81% | 87% | 85% | 75% | 86% |

N/A - Not available.

2. UVB Studies

The purpose of this study was to determine the effectiveness of sunscreen formulations in inhibiting UVB (290–320 nm) sunburn cell production. Similar materials and methods and procedures were used in conducting the experiments. However, no 8-MOP was used in the studies and light Source 3 was used.

a. Results

The results from the studies are presented in Table VI and are presented as the total number of sunburn cells per 20 fields. Animals were irradiated as described, with or without prior application of the indicated sunscreen formulation. Each experiment utilized two mice, designated A or B. A Protective Index (% reduction of SBC formation) was calculated as:

$$\text{Protective Index} = \frac{(\text{Irradiated Untreated} - \text{Product})}{(\text{Irradiated Untreated})} \times 100$$

b. Conclusions

As shown in Table V, UVB irradiation of untreated skin produced a very marked increase in sunburn cells compared to unirradiated samples as expected. Sunburn cells may be found in most fields at 40× magnification after irradiation, but they are found much less frequently in skin which had an effective UVB sunscreen formulation applied before irradiation.

The results of the experiment are highlighted in the following Tables:

TABLE VII

Results for UVA Radiation

| Product Tested | Number of Sunburn Cells | Percent Reduction in Comparison to Controls |
|---|---|---|
| Untreated Unirradiated | 3 | Control |
| Untreated Irradiated | 95 | Control |
| Formula 302 includes 8% Proteinaceous Emulsifier 1 | 35.4 | 62.74% |
| Formula 3010 includes 2% Proteinaceous Emulsifier 3 | 17.6 | 81.47% |
| Formula 3010 includes 8% Proteinaceous Emulsifier 3 | 12.6 | 87.00% |
| Formula 3012 includes 10% Proteinaceous Emulsifier 1 + 4% Benzophenone | 16.2 | 82.95% |
| Formula 3014 includes 4% TiO$_2$ | 14.0 | 85.26% |
| Formula 3016 includes 4% TiO$_2$ + 2% Proteinaceous Emulsifier 3 | 8.8 | 90.74% |

TABLE VI

| Animal | Irradiated No Sunscreen | Unirradiated No sunscreen | PM-P2 | MOSFP1 | MOSF3P | Photoplex |
|---|---|---|---|---|---|---|
| A | 67 | 03 | 23 | 37 | 09 | 06 |
| B | 59 | 04 | 08 | 60 | 30 | 10 |
| TOTAL | 126 | 07 | 31 | 97 | 39 | 16 |
| MEAN | 63 | 04 | 16 | 49 | 20 | 08 |
| PERCENT REDUCTION | — | — | 75% | 48% | 22% | 92% |

TABLE VIII

Results for UVB Radiation

| Product Tested | Number of Sunburn Cells | Percent Reduction in Comparison to Controls |
| --- | --- | --- |
| Untreated Unirradiated | 3.5 | Control |
| Untreated Irradiated | 63 | Control |
| Formula MOSFP1 includes 2% Proteinaceous Emulsifier 2 | 49 | 22.22% |
| Formula MOSF3P includes 8% Proteinaceous Emulsifier 2 + 6% $TiO_2$ | 20 | 68.25% |
| 7% Parsol MCX | 15 | 76.19% |
| Photoplex | 12 | 80.95% |

III. LANGERHANS CELLS STUDIES

As discussed above, we expect to see a protective effect on Langerhans cells through use of the proteinaceous materials of the present invention. In order to determine the extent of the protective effect, the following procedure will be used:

A similar UV exposure regimen is employed as was used in the UVA and UVB studies discussed above. Specimens of epidermis are obtained by removing the roofs of vacuum-induced blisters (Klistala U, et al. "Dermo-epidermal Separation with Suction" *J. Invest. Dermatol.* 48:466–477 (1967)) from the UV-treated sites and, in some instances, from an additional untreated site. Blisters can be raised from each treatment site, one immediately after UV exposure, and another one week after UV exposure.

Langerhans cells can then be identified and counted using an HLA-DR-positive and CD1a-positive cell assay. In the assay, portions from the face of each blister is tested in immunofluorescence using anti-HLA-DR (Becton Dickinson, Sunnyvale, Calif., USA) and anti-CD1a (OKT6, Ortho Pharmaceuticals, Raritan, N.J., USA) monoclonal antibodies. Elmets CA, et al. "Differential Distribution of Langerhans Cell in Organ Culture of Human Skin" *J. Invest. Dermatol.* 79:340–345 (1982), the disclosure of which is hereby incorporated by reference. Counting of the Langerhans cells is accomplished by quantifying the mean number of HLA-DR-positive and CD1a-positive Langerhans cells per $mm^2$. Five high-power (400×) microscopic fields can be examined by immunofluorescence, for example, using a Nikon immunofluorescence microscope equipped with epi-fluorescence. All specimens are examined in a blinded fashion. The presence of positively stained cell bodies is used as the criterion by which cells are counted.

It is expected that skin treated with UV radiation and formulations containing the proteinaceous materials of the present invention will possess more normal populations of healthy Langerhans cells as compared to untreated skin. In irradiated but untreated skin there is typically a depletion in the population of Langerhans cells, as well as the effect that the existing Langerhans cells appear abnormal. Further, it is possible that repopulation of Langerhans cells will be stimulated by the proteinaceous materials of the present invention.

A variety of papers have been cited herein and they are hereby expressly incorporated by reference. Further, it will be appreciated that a variety of different protocols and compositions could be used without departing from the ambit of the present invention. Therefore, no matter how detailed the foregoing may appear in text, the scope of the present invention should only be construed in light of the appended claims and any equivalents thereof.

APPENDIX I

| INGREDIENTS % | Formula # | | | | | | | | | | | | | | | | | | |
| --- | --- | --- | --- | --- | --- | --- | --- | --- | --- | --- | --- | --- | --- | --- | --- | --- | --- | --- | --- |
| | 301 | 302 | 303 | 304 | 305 | 306 | 307 | 308 | 309 | 3010 | 3011 | 3012 | 3013 | 3014 | 3015 | 3016 | 3017 | 3018 | 3019 |
| Water + 1% Keltrol | q.s. | q.s. | q.s. | q.s. | ? | q.s. | q.s. | q.s. | q.s. | ? | q.s. | q.s. | q.s. | 60.0 | ? | 60.0 | 57.0 | 57.0 | 58.0 |
| EDTA | 0.1 | 0.1 | 0.1 | 0.1 | ? | 0.1 | 0.1 | 0.1 | 0.1 | ? | 0.1 | 0.1 | 0.1 | 0.1 | ? | 0.1 | 0.1 | 0.1 | 0.1 |
| NaOH 50% | 0.1 | 0.1 | 0.1 | 0.1 | ? | 0.1 | 0.1 | 0.1 | 0.1 | ? | 0.1 | 0.1 | 0.1 | 0.1 | ? | 0.06 | 0.06 | 0.06 | 0.06 |
| Germaben ™ 2e | 1.0 | 1.0 | 1.0 | 1.0 | ? | 1.0 | 1.0 | 1.0 | 1.0 | ? | 1.0 | 1.0 | 1.0 | 1.0 | ? | 1.0 | 1.0 | 1.0 | 1.0 |
| Proteinaceous Emulsifier 1[1] | 8.0 | 8.0 | 15.0 | 15.0 | 10.0 | 10.0 | 10.0 | — | — | ? | 10.0 | 10.0 | 10.0 | — | ? | — | — | 20.0 | 15.0 |
| Elefac ™[2] | 9.0 | 9.0 | 10.0 | 10.0 | 10.0 | — | — | 10.0 | 10.0 | ? | 10.0 | 10.0 | 10.0 | 10.0 | 10.0 | 15.0 | — | 10.0 | 10.0 |
| Oat Oil | 10.0 | 10.0 | 12.0 | 12.0 | 10.0 | — | — | — | — | ? | 10.0 | 10.0 | 10.0 | 12.0 | 12.0 | 15.0 | 15.0 | 10.0 | 10.0 |
| Ganex ™ 216 | 2.0 | 2.0 | 2.0 | 2.0 | 2.0 | — | — | 1.0 | 1.0 | ? | 2.0 | 2.0 | 2.0 | 2.0 | 2.0 | 2.0 | 15.0 | 2.0 | 2.0 |
| $TiO_2$ | — | — | — | — | 7.0 | 5.0 | — | — | — | ? | — | — | — | 4.0 | 7.0 | 4.0 | 2.0 | — | 4.0 |
| Pemulan ™[3] | 0.1 | 0.1 | 0.1 | 0.1 | 0.1 | — | — | 0.1 | 0.1 | ? | 0.1 | 0.1 | 0.1 | 0.1 | 0.1 | 0.1 | 0.1 | 0.1 | 0.1 |
| Parsol MCX ™[4] | — | — | — | — | ? | — | 7.0 | — | — | ? | — | — | — | — | ? | — | 4.0 | 6.0 | — |
| Proteinaceous Emulsifier 2[5] | — | — | — | — | ? | — | — | 2.0 | 0.2 | 8.0 | — | — | — | — | ? | 2.0 | 2.0 | — | — |
| Isopropylpalmitate | — | — | — | — | ? | — | — | 10.0 | 10.0 | ? | — | — | — | — | ? | — | — | — | — |

APPENDIX I-continued

| INGREDIENTS % | Formula # | | | | | | | | | | | | | | | | | | |
|---|---|---|---|---|---|---|---|---|---|---|---|---|---|---|---|---|---|---|---|
| | 301 | 302 | 303 | 304 | 305 | 306 | 307 | 308 | 309 | 3010 | 3011 | 3012 | 3013 | 3014 | 3015 | 3016 | 3017 | 3018 | 3019 |
| Benzophenone | — | — | — | — | ? | — | — | — | — | ? | 4.0 | 4.0 | — | — | ? | — | — | — | — |
| Proteinaceous Emulsifer 3[6] | — | — | — | — | ? | — | — | — | — | ? | — | — | — | — | ? | 2.0 | 2.0 | — | — |

[1] Proteinaceous Emulsifier 1 is derived from the fines prepared in accordance with Example I in U.S. Pat. application Ser. No. 08/031,611.
[2] Elefac is a light ester, octyldodecyl neopentanoate (Bernel Chemical, Engelwood, NJ) used as a wetting agent.
[3] Pemulan is an acrylate emulsifier, including $C_{10}$–$C_{30}$ alkyl acrylate cross polymers (B.F. Goodrich, Brecksville, OH).
[4] Parsol MCX is a sunscreen, including octyl methoxycinnamate (Givaudan-Roure, Teaneck, NJ).
[5] Proteinaceous Emulsifier 2 is derived from the roughs prepared in accordance with Example I in U.S. Pat. application Ser. No. 08/031,611 and heating them to at least 60° C.
[6] Proteinaceous Emulsifier 3 is derived from the roughs prepared in accordance with Example I in U.S. Pat. application Ser. No. 08/031,611.

APPENDIX II

| INGREDIENTS (%) | Formula # OM-P2 |
|---|---|
| DI Water | 67.0 |
| Proplylene Glycol | 5.0 |
| Hydroxypropyl Methocal | 0.1 |
| EDTA | 0.05 |
| AMP[1] | 0.25 |
| Germaben 2e | 0.8 |
| Fintex (Finsolv T) | 5.0 |
| Tween 80 | 0.1 |
| Pemulan | 0.2 |
| Carbopol 2984 | 0.2 |
| Proteinaceous Emulsifier 3 | 8.0 |
| $TiO_2$ + Isopropyl Palmitate | 16.0 |
| Tween 85 | 1.0 |

[1] AMP is aminomethyl propanol, a pH adjuster.

APPENDIX III

| INGREDIENTS (%) | Formula # | |
|---|---|---|
| | MOSF-1P | MOSF-3P |
| Dimethicone | 1.0 | 1.0 |
| Finsolv T | 2.0 | 3.0 |
| Isopropyl Palmitate | 2.0 | 2.0 |
| Triglyceride | 3.0 | 3.0 |
| Ceraphyl GA | 3.0 | 3.0 |
| Pemulan TPI | 0.2 | 0.2 |
| Vitamin A | 0.2 | 0.2 |
| Proteinaceous Emulsifier 3 | 2.0 | 0.2 |
| Water | 80.0 | 80.0 |
| Glycerine | 4.0 | 4.0 |
| Polysorbate 80 | 0.4 | 0.4 |
| Germaben 2e | 1.0 | 1.0 |
| EDTA | 0.1 | 0.1 |
| Panthenol | 1.0 | — |
| CMC[1] | 0.1 | — |
| Carbopol 981 | 0.3 | 0.3 |
| Triethanolamine | 0.4 | 0.4 |

[1] CMC is a cellulose gum (Aqualon, Wilmington, DE).

What we claim is:

1. A method for reducing the formation of sunburn cells in mammalian skin, comprising applying a topical formulation comprising an amount of a free flowing seed derived material having a protein content of between about 1% to 50% and an average particle size of from about 1.0 μm to 600 μm to skin prior to exposing the skin to ultraviolet radiation.

2. The method of claim 1, further comprising heating the formulation to a temperature of at least 60° C. prior to application to the skin.

3. A method for inhibiting the formation of sunburn cells in skin when the skin is exposed to ultraviolet radiation, comprising applying a composition including a sunburn cell protective amount of a substantially chemically intact proteinaceous particulate material derived from seeds in a topically acceptable carrier to the skin prior to exposure to ultraviolet radiation.

4. The method of claim 3, wherein the seeds are selected from the group consisting of legumes and grains.

5. The method of claim 4, wherein the seeds are oats.

6. The method of claim 3, wherein the proteinaceous material is derived from grinding the seeds and extracting lipids from the resulting ground material with an organic solvent.

7. The method of claim 3, wherein the formation of sunburn cells is reduced by greater than about 50 percent relative to untreated skin.

8. The method of claim 3, wherein the proteinaceous particulate material is heated to about 60° C. prior to incorporation in the carrier.

* * * * *